United States Patent
Ribery et al.

[11] Patent Number: 6,139,824
[45] Date of Patent: Oct. 31, 2000

[54] DEODORANT COMPOSITION

[75] Inventors: Delphine Ribery, Levallois Perret; Lionnel Aubert, Domont, both of France

[73] Assignee: L'Oreal S.A., Paris, France

[21] Appl. No.: 09/356,883

[22] Filed: Jul. 19, 1999

[30] Foreign Application Priority Data

Jul. 17, 1998 [FR] France ................................ 98 09155
Oct. 13, 1998 [FR] France ................................ 98 12802

[51] Int. Cl.$^7$ .............................. A61K 7/32; A61K 7/34; A61K 7/36; A61K 7/38; A61K 7/00
[52] U.S. Cl. .............................. 424/65; 424/66; 424/67; 424/68; 424/400; 424/401; 514/785; 514/938
[58] Field of Search .................................. 424/65, 66, 67, 424/68, 400, 401; 252/309; 514/785, 938

[56] References Cited

U.S. PATENT DOCUMENTS

| | | | |
|---|---|---|---|
| 3,792,068 | 2/1974 | Luedders et al. | 424/65 |
| 4,920,158 | 4/1990 | Murray et al. | 524/22 |
| 5,162,378 | 11/1992 | Guthauser | 514/785 |
| 5,635,165 | 6/1997 | Panitch | 424/65 |
| 5,656,280 | 8/1997 | Herb et al. | 424/401 |

FOREIGN PATENT DOCUMENTS

| | | |
|---|---|---|
| 1087261A | 6/1994 | China . |
| 0 091 368 | 10/1983 | European Pat. Off. . |
| 0 157 736 | 10/1985 | European Pat. Off. . |
| 0 593 657 | 4/1994 | European Pat. Off. . |
| 2 201 880 | 5/1974 | France . |
| 2 551 658 | 3/1985 | France . |
| 2 575 922 | 7/1986 | France . |
| 58-57313 | 4/1983 | Japan . |
| 58-83612 | 5/1983 | Japan . |
| 59-36607 | 2/1984 | Japan . |
| 60-239411 | 11/1985 | Japan . |
| 61-1002 | 1/1986 | Japan . |
| 2-31688 | 2/1990 | Japan . |
| 2-111714 | 4/1990 | Japan . |
| 3-110013 | 5/1991 | Japan . |
| 4-103519 | 4/1992 | Japan . |
| WO 96/00566 | 1/1996 | WIPO . |
| WO 97/06777 | 2/1997 | WIPO . |

OTHER PUBLICATIONS

Encyclopedia of Chemical Technology, $4^{th}$ Edition, vol. 2, pp. 330–337.
English language Derwent Abstract of EP 0 091 368, Oct. 12, 1983.
English language Derwent Abstract of EP 0 157 736, Oct. 9, 1985.
English language Derwent Abstract of EP 0 593 657, Apr. 27, 1994.
English language Derwent Abstract of FR 2 201 880, May 3, 1974.
English language Derwent Abstract of FR 2 551 658, Mar. 15, 1985.
English language Derwent Abstract of FR 2 575 922, Jul. 18, 1986.
English language Derwent Abstract of JP 58–57313, Apr. 5, 1983.
English language Derwent Abstract of JP 58–83612, May 19, 1983.
English language Derwent Abstract of CN 1087261A, Jun. 1, 1994.
English language Derwent Abstract of JP 59–36607, Feb. 28, 1984.
English language Derwent Abstract of JP 60–239411, Nov. 28, 1985.
English language Derwent Abstract of JP 61–1002, Jan. 7, 1986.
English language Derwent Abstract of JP 2–31688, Feb. 1, 1990.
English language Derwent Abstract of JP 2–111714, Apr. 24, 1990.
English language Derwent Abstract of JP 3–110013, May 10, 1991.
English language Derwent Abstract of JP4–103519, Apr. 6, 1992.

*Primary Examiner*—Shelley A. Dodson
*Attorney, Agent, or Firm*—Finnegan, Henderson, Farabow, Garrett & Dunner, L.L.P.

[57] ABSTRACT

A deodorant composition in the form of a water-in-oil emulsion comprising an effective amount of at least one alum salt dissolved in the aqueous phase of the said emulsion. A process for treating human underarm odors using the present deodorant composition.

37 Claims, No Drawings

DEODORANT COMPOSITION

The present invention relates to a deodorant composition in the form of a water-in-oil emulsion comprising an effective amount of at least one alum salt dissolved in the aqueous phase of the composition.

The present invention also relates to a deodorization process using the composition and more especially to a process for treating human underarm odors, which comprises applying an effective amount of the composition to the armpit area.

In the cosmetic field, it is a well-known practice to use, in topical application, deodorant products containing active substances of antiperspirant type or of bactericidal type to reduce or even eliminate the generally unpleasant underarm odors.

Antiperspirants have the effect of limiting the flow of sweat. They generally consist of aluminium salts which, on the one hand, are skin irritants and, on the other hand, reduce the flow of sweat by modifying the skin physiology, which is unsatisfactory.

Bactericides inhibit the growth of the skin flora responsible for underarm odors. Among the bactericidal products, the most commonly used is Triclosan (5-chloro-2-(2,4-dichlorophenoxy)phenol), which has the drawback of considerably modifying the ecology of the skin flora and of being inhibited by certain compounds such as, for example, nonionic surfactants, which are commonly used in the formulation of cosmetic compositions. The insoluble nature of Triclosan in water does not allow it to be incorporated into essentially aqueous formulations.

With the aim of obtaining long-term efficacy, products are sought which exert the action of a deodorant active agent, i.e. products which are capable of modifying, reducing and/or eliminating or preventing the development of body odor (this definition is given in the book "Cosmetic Science and Technology Series"—1988/Volume 7, chapter 10—IIIc). In addition, products are sought which do not have the drawbacks of the active substances used in the prior art.

It is known that certain aluminium salts have good deodorant properties and are better tolerated than the active agents mentioned above. This is the case, for example, for alums such as potassium alum or ammonium alum, which have been known for a long time as bactericidal active agents and astringents.

Various types of formulation based on these active agents have been used for many years.

Deodorant compositions molded from blocks of alum in crude form are known in patents EP-B-157,736 and U.S. Pat. No. 5,399,364. These formulations are uncomfortable to apply, difficult to spread on the skin and need to be made wet frequently with water before application, to obtain low efficacy. Moreover, these products do not allow other cosmetic additives to be introduced.

Anhydrous deodorant compositions in the form of anhydrous powders or dispersions containing an alum salt in dry or non-dissolved form are also known in the prior art, such as those described in patent applications JP 04,103,519, JP 60,239,411, EP-A-0,593,657, JP 58,057,313 and EP-A-0, 091,368. Sticks molded from a ground pure alum and from a plasticizer such as glycerol or sorbitol are also known in patent application WO 96/00566. This type of composition has the drawback of being uncomfortable to use since it lacks a sensation of freshness. Moreover, these formulations based on alum in powder form are difficult to produce on account of a homogeneity which is difficult to control.

To overcome these drawbacks, aqueous deodorant formulations in which the alum is dissolved in the aqueous phase have been produced. Aqueous or aqueous-alcoholic solutions based on potassium alum are known in particular in patent applications FR-A-2,551,658, CN 1,087,261, FR-A-2,575,922 and FR-A-2,201,880. Oil-in-water emulsions containing potassium or ammonium alum dissolved in the aqueous phase are also known in Japanese patent applications Hei 2-111,714, Sho 59-36607, Sho-58-83612 and Hei 3-110,013. Formulations containing three immiscible phases which can contain alum dissolved in an aqueous phase are also known in Japanese patent applications Hei 2-31688 and Sho 61-1002.

All these aqueous deodorant formulations in which the alum is dissolved have the drawback that this type of active agent cannot be used in concentrations above its solubility in water in order to obtain optimum deodorant efficacy. Now, the alums most commonly used in cosmetics, such as potassium alum or ammonium alum, have low solubility in water (i.e.: 11.4% by weight and 12% by weight, respectively, at 20° C., according to the "Encyclopedia of Chemical Technology; 4th Edition, Volume 2; pages 330–337") and cannot be used in these aqueous deodorant compositions above this amount, beyond which an undesirable recrystallization phenomenon is observed during storage according to the standard tests for storing cosmetic products (i.e. after storage for 2 months at 4° C., at room temperature and at 45° C.). This recrystallization has the consequence of producing cosmetic products of heterogeneous appearance.

The inventors have discovered, surprisingly, that supports of the water-in-oil emulsion type can contain alums, and more particularly those of low solubility in water, dissolved in the aqueous phase in concentrations above their solubility without observing a recrystallization of the alum during their storage according to the standard tests for storing cosmetic products.

This discovery forms the basis of the invention.

Thus, in accordance with one of the subjects of the present invention, novel deodorant compositions are now proposed, which are essentially characterized in that they are in the form of a water-in-oil emulsion containing an effective amount of at least one alum dissolved in the aqueous phase of the said emulsion.

The expression "effective amount of alum" means an amount of alum, in the pharmaceutical form used, which is sufficient to produce a satisfactory deodorant effect after application.

The expression "deodorant effect" means an activity of substantially reducing or even eliminating unpleasant odors and more particularly body odor.

Another subject of the invention also relates to the use of the inventive compositions for the manufacture of deodorant cosmetic products intended for treating human underarm odors.

Another subject of the invention is novel cosmetic or dermatological deodorant formulations which include a composition as defined above.

Another subject of the invention is a deodorization process using the inventive composition, and more particularly a process for treating human underarm odors, which comprises applying an effective amount of the composition to the armpit area.

Another subject of the invention is the use of a support of the water-in-oil emulsion type for the manufacture of cosmetic or dermatological aqueous deodorant products containing at least one alum salt dissolved in an amount, relative to the water, above the solubility in water of the said alum.

Other subjects will become apparent in the light of the description and the examples which follow.

In accordance with the present invention, the alums which can be used are preferably chosen from:

potassium alum, of structure: $KAl(SO_4)_2.12H_2O$
ammonium alum, of structure: $NH_4Al(SO_4)_2.12H_2O$
sodium alum, of structure: $NaAl(SO_4)_2.12H_2O$
the aluminium sulphate salts of structure: $Al_2(SO_4)_3.nH_2O$ in which n is from 0 to 27

The compositions according to the invention are more particularly suitable for alums of low solubility in water, and in particular those which have a solubility of less than 30 g/100 ml of water at 20° C. and more particularly a solubility in water of less than 13 g/100 ml of water at 20° C., such as:

potassium alum (11.4 g/100 ml of water at 20° C.),
ammonium alum (12 g/100 ml of water at 20° C.).

Potassium alum is preferred, and especially the commercial product sold by the company Giulini Chemie (Warwick Chimilux SA).

The alums are dissolved in the aqueous phase of the compositions in accordance with the invention in concentrations preferably ranging from 0.5 to 30% by weight relative to the total weight of the composition. Needless to say, the concentration of the alum active agent varies depending on the pharmaceutical form chosen. It can preferably range from 1 to 20% by weight for formulations in the form of sticks, creams, gels or roll-ons. It can preferably range from 1 to 15% by weight for formulations packaged in aerosol devices.

In one particularly preferred form of the invention, the alum salt will be present in the aqueous phase in a concentration of greater than 10% by weight and more preferably greater than or equal to 15% by weight.

The compositions according to the invention comprise a fatty phase which can include one or more fatty substances comprising one or more oils and/or one or more waxes. The term "oil" means a compound which is liquid at room temperature. The term "wax" means a compound which is solid or substantially solid at room temperature and whose melting point is generally greater than 35° C.

Preferably, the oils are mineral oils (vaseline), plant oils (sweet almond oil, macadamia oil, blackcurrant seed oil, jojoba oil), synthetic oils such as perhydrosqualene, fatty alcohols, fatty acids or fatty esters (such as the $C_{12}$–$C_{15}$ alkyl benzoate sold under the trade name "Finsolv TN" by the company Finetex), octyl palmitate, isopropyl lanolate, triglycerides, including capric/caprylic acid triglycerides, oxyethylenated or oxypropylenated fatty esters and ethers, fluoro oils, perfluoro oils or polyalkylenes such as polydecenes.

Waxy compounds are preferably animal, fossil, plant, mineral or synthetic waxes and hydrogenated castor oil. Mention may be made in particular of beeswaxes, carnauba wax, candelilla wax, sugar cane wax, Japan wax, ozokerites, montan wax, microcrystalline waxes, paraffins, polyethylene waxes and silicone waxes and resins.

The fatty phase can also comprise a volatile or non-volatile silicone oil, such as cyclomethicones or dimethicones. A volatile silicone oil such as, for example, the cyclomethicones sold under the trade names "DC245 Fluid" or "DC 246 Fluid" by Dow Corning can be used, for example, in the compositions of the present invention.

The fatty phase is preferably present in the compositions in weight concentrations ranging from 5% to 80% relative to the total weight of the composition, and preferably in weight compositions ranging from 10% to 50% relative to the total weight of the composition.

The aqueous phase of these emulsions can contain ingredients other than water, for instance wetting agents such as polyols, stabilizers such as citric acid or lactic acid, and sequestering agents (ethylenediamine tetraacetic acid).

In a known manner, the emulsion according to the invention can contain one or more water-in-oil-emulsion emulsifying surfactants (which will be referred to hereinbelow as W/O emulsifiers). Any cosmetic emulsifier generally having an HLB (hydrophilic-lipophilic balance) of less than or equal to 6 can be used as W/O emulsifiers in the invention. Mention may be made, for example, of fatty acid esters of glucose such as methylglucose dioleate, fatty acid esters of glycerol such as glyceryl isostearate, glyceryl oleate and glyceryl ricinoleate, fatty acid esters of sorbitol such as sorbitan tristearate and sorbitan di- or trioleate; polyalkylpolyethersiloxanes bearing polyoxyalkylenated groups grafted onto the main silicone chain. Polyalkylpolyethersiloxanes bearing polyoxyalkylenated groups grafted onto the main silicone chain will preferably be used.

Among the silicone W/O emulsifiers which will be used more particularly are those chosen from the group formed by the polydiorganosiloxanes of formulae (I) and (II) below, it being possible for these compounds to be dispersed in a volatile dimethicone,

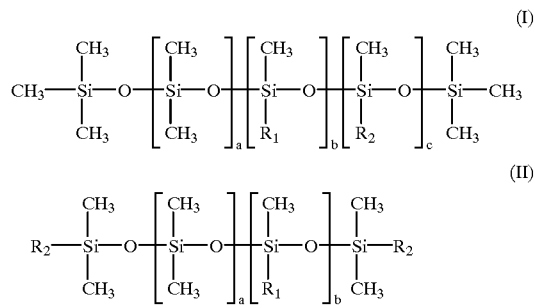

in which:

$R_1$ is chosen from linear and branched $C_{12}$–$C_{20}$ and preferably $C_{12}$–$C_{18}$ alkyl groups;

$R_2$ is chosen from the group:

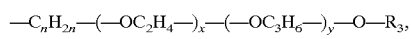

| | |
|---|---|
| $R_3$ | is chosen from a hydrogen atom, and linear and branched alkyl radicals comprising from 1 to about 12 carbon atoms, |
| a | is an integer ranging from 0 to about 500, |
| b | is an integer ranging from 0 to about 500, |
| c | is an integer ranging from 1 to about 500, |
| n | is an integer ranging from 2 to 12, | x and y are each an integer ranging from 0 to about 50, the sum x+y being greater than or equal to the value 1.

Among the preferred emulsifying polyorganosiloxanes are those of formula (I) in which a is an integer ranging from 2 to 450, b is equal to 0, c is an integer ranging from 2 to 40, n is an integer ranging from 2 to 5, x is an integer ranging from 1 to 30 and y is an integer ranging from 0 to 30, with $x \geq y$. Among these silicone emulsifiers, one which can be used more particularly is the mixture of cyclomethicone and dimethicone copolyol (CTFA name), such as the product sold by the company Dow Corning under the trade name Silicone DC 3225 C or the product sold by the company Goldschmidt under the name Abil EM 97.

Among the preferred emulsifying polyorganosiloxanes are those of the formula (I) in which a is equal to 0 and b is other than 0, such as, more particularly, laurylmethicone copolyol (CTFA nomenclature—7th Edition—1997) sold by the company Dow Corning under the trade name QT-5200 Formulation Aid, or the cetyidimethicone copolyol which is sold, for example, under the names "Abil WE09®" and "Abil EM90®" by the company Goldschmidt.

In the compositions according to the invention, the W/O emulsifying surfactant is preferably present in weight proportions ranging from about 0.1% to about 10% and preferably ranging from about 1% to about 8% relative to the total weight of the composition.

The deodorant compositions of the present invention can also comprise other standard deodorant active agents in addition to the alum.

These deodorant active agents can be chosen, for example, from: water-soluble zinc salts such as, for example, zinc pyrrolidonecarboxylate (more commonly known as zinc pidolate), zinc sulphate, zinc chloride, zinc lactate, zinc gluconate and zinc phenolsulphonate; aluminium salts such as, for example, aluminium chloride and aluminium hydroxyhalides; zirconium salts such as, for example, zirconium oxide salts and hydroxyzirconyl salts; complexes of metals such as aluminium or zirconium with an amino acid such as, for example, glycine, as described in U.S. Pat. No. 3,792,068; bactericides.

The compositions of the invention can also comprise cosmetic adjuvants chosen from fatty substances, organic solvents, gelling agents, emollients, softeners, antioxidants, opacifiers, stabilizers, silicones, antifoaming agents, hydrating agents, vitamins, fragrances, preserving agents, surfactants, fillers, sequestering agents, polymers, propellants, acidifying or basifying agents, dyes, pigments, thickeners and any other ingredient usually used in cosmetics.

The surfactants are preferably chosen from nonionic surfactants such as, for example, the products of condensation of a fatty alcohol or of a fatty acid with a polyalkylene glycol chain.

The thickeners, which are preferably nonionic, can be chosen from modified and unmodified guar gums and celluloses, such as hydroxypropyl guar gum and cetylhydroxyethylcellulose, and hectorites such as, for example, Bentone Gel MiO sold by the company NL Industries or the silica Aerosil R 972 sold by the company Degussa.

As mentioned, the compositions of the invention can also comprise emollients, which contribute a soft, dry, non-sticky sensation when the composition is applied to the skin. These emollients can be chosen from products such as volatile silicones, non-volatile silicones and other non-volatile emollients.

Volatile silicones are defined, in a known manner, as compounds which are volatile at room temperature. Among these compounds, some which may be mentioned are cyclic and linear volatile silicones of the dimethylsiloxane type in which the chains comprise from 3 to 9 silicone residues. The cyclomethicones D4 or D5 are preferably chosen.

Non-volatile silicones are defined, in a known manner, as compounds of low vapour pressure at room temperature. Among these compounds are included: polyalkylsiloxanes, in particular linear polyalkylsiloxanes such as, for example, polydimethylsiloxanes, or linear dimethicones sold by the company Dow Corning under the name "Dow Corning 200 Fluid"; polyalkylarylsiloxanes such as, for example, the polymethylphenylsiloxanes sold by the company Dow Corning under the name "Dow Corning 556 Fluid"; copolymers of polyether and of siloxane, such as, for example, dimethicone copolyols.

The non-volatile emollients which can be used in the present invention are preferably: hydrocarbon-based derivatives, mineral oils, fatty alcohols, esters of $C_3$–$C_{18}$ alcohols with $C_3$–$C_{18}$ acids, esters of benzoic acid with $C_{12}$–$C_{18}$ alcohols and mixtures thereof, $C_2$–$C_6$ polyols preferably chosen from glycerol, propylene glycol and sorbitol, and polyalkylene glycol polymers.

When the deodorant compositions according to the invention are intended for cosmetic use, they can be in the form of lotions, creams or fluid gels dispensed as an aerosol spray, in a pump-dispenser bottle or as a roll-on, in the form of thickened creams dispensed in tubes and in the form of sticks, and contain, in this respect, the ingredients and propellants generally used in products of this type and which are well known to those skilled in the art, provided that they do not interfere with the alums described in the present invention.

The invention can also find advantageous applications in the field of various deodorants and maintenance products (ambient air, textiles, refrigerators, dustbin wagons, dustbins, pet litters and cages or the ventilation cladding of buildings).

Concrete, but in no way limiting, examples illustrating the invention will now be given.

EXAMPLE 1

Deodorant Stick According to the Invention

| Ingredients | % by weight |
| --- | --- |
| Laurylmethicone copolyol sold by the company Dow Corning under the name Q2-5200 Formulation Aid | 5.00 |
| Antioxidant | 0.05 |
| Cyclohexadimethylsiloxane sold by the company Dow Corning under the name Dow Corning 246 Fluid | 22.50 |
| Polyethylene wax sold by the company Petrolite under the name Polywax 500 Polyethylene | 12.5 |
| Potassium alum sold by the company Giulini Chemie (Warwick Chimilux SA) | 15.00 (i.e. 33.3% by weight relative to the amount of water) |
| Demineralized water | 44.95 |

The composition has good deodorant efficacy and remains stable after storage for 2 months at 4° C., at room temperature and at 45° C. without formation of alum crystals.

EXAMPLE 2

Deodorant Cream According to the Invention

| Ingredients | % by weight |
| --- | --- |
| Laurylmethicone copolyol sold by the company Dow Corning under the name Q2-5200 Formulation Aid | 2.00 |
| Isopropyl myristate | 15.00 |
| Potassium alum sold by the company Giulini Chemie (Warwick Chimilux SA) | 10.00 (i.e. 13.6% by weight relative to the amount of water) |
| Demineralized water | 73.00 |

EXAMPLE 3 (COMPARATIVE)
Aqueous Solution of Alum at 13.6% by Weight

| Ingredients | % by weight |
| --- | --- |
| Potassium alum sold by the company Giulini Chemie (Warwick Chimilux SA) | 13.60 |
| Demineralized water qs | 100 |

This composition comprises the alum dissolved in the same concentration relative to the amount of water (i.e. 13.6% by weight) as that used for the composition of Example 2. After storage for 3 days at room temperature the presence of alum crystals begins to be observed.

EXAMPLE 4 (COMPARATIVE)
O/W Emulsion Deodorant Roll-On Containing 10% Potassium Alum

| Ingredients | % by weight |
| --- | --- |
| Cetylstearyl alcohol sold by the company Condea under the trade name Nafol 1618F | 2.5 |
| Oxyethylenated (33 EO) cetylstearyl alcohol sold by the company Condea under the trade name Emuldac AS 25 | 1.25 |
| Sorbitan monostearate sold by the company ICI under the trade name Tween 60 | 2.2 |
| Stearyl alcohol sold by the company Aegis Chemical under the trade name Acilol 18 | 0.3 |
| Isohexadecane sold by the company Bayer | 6 |
| Propylene glycol sold by the company BASF | 3 |
| Methyl paraben sold by the company Unipex | 0.1 |
| Potassium alum sold by the company Giulini Chemie (Warwick Chimilux SA) | 10.15 (i.e. 13.6% by weight relative to the amount of water) |
| Demineralized water | 74.50 |

This aqueous continuous emulsion comprises the alum dissolved in the same concentration relative to the amount of water (i.e. 13.6% by weight) as that in the composition of Example 2. It is unstable. After storage for 2 months at 4° C. and at room temperature, the presence of alum crystals and phase separation of the formulation are observed.

EXAMPLE 5
Deodorant Cream According to the Invention

| Ingredients | % by weight |
| --- | --- |
| Laurylmethicone copolyol sold by the company Dow Corning under the name Q2-5200 Formulation Aid | 2.00 |
| Isopropyl myristate | 15.00 |
| Potassium alum sold by the company Giulini Chemie (Warwick Chimilux SA) | 15.00 (i.e. 22% by weight relative to the amount of water) |
| Demineralized water | 68.00 |

The composition has good deodorant efficacy and remains stable after storage for 2 months at 4° C., at room temperature and at 45° C. without formation of alum crystals.

EXAMPLE 6 (COMPARATIVE)
Aqueous Solution of Alum at 22% by Weight

| Ingredients | % by weight |
| --- | --- |
| Potassium alum sold by the company Giulini Chemie (Warwick Chimilux SA) | 22.00 |
| Demineralized water qs | 100.00 |

EXAMPLE 7 (COMPARATIVE)
O/W Emulsion Deodorant Roll-On Containing 15% of Potassium Alum

| Ingredients | % by weight |
| --- | --- |
| Cetylstearyl alcohol sold by the company Condea under the trade name Nafol 1618 F | 2.5 |
| Oxyethylenated (33 EO) cetylstearyl alcohol sold by the company Condea under the trade name Emuldac AS 25 | 1.25 |
| Sorbitan monostearate sold by the company ICI under the trade name Tween 60 | 2.2 |
| Stearyl alcohol sold by the company Aegis Chemical under the trade name Acilol 18 | 0.3 |
| Isohexadecane sold by the company Bayer | 6 |
| Propylene glycol sold by the company BASF | 3 |
| Methyl paraben sold by the company Unipex | 0.1 |
| Potassium alum sold by the company Giulini Chemie (Warwick Chimilux SA) | 15.55 (i.e. 22% by weight relative to the amount of water) |
| Demineralized water | 69.1 |

This aqueous continuous emulsion comprises the alum dissolved in the same concentration relative to the amount of water (i.e.: 22% by weight) as that in the composition of Example 5. It is unstable. After storage for 2 months at 4° C. and at room temperature, the presence of alum crystals and phase separation of the formulation are observed.

EXAMPLE 8
Aerosol Composition According to the Invention

| | % by weight |
| --- | --- |
| Ingredients in the formulation of the aerosol formulation fluid | |
| Dimethicone copolyol mixture sold by the company Dow Corning under the name Q2-3225C | 9.1 |
| Cyclopentadimethylsiloxane sold by the company Dow Corning under the name Dow Corning 245 Fluid | 9.1 |
| Potassium alum sold by the company Giulini Chemie (Warwick Chimilux SA) | 15.00 (i.e. 22.4% relative to the amount of water) |
| Demineralized water | 66.8 |
| Composition of the aerosol formulation | |
| Fluid | 45 |
| Isobutane (propellant) | 55 |

The composition has good deodorant efficacy and remains stable after storage for 2 months at 4° C., at room temperature and at 45° C. without formation of alum crystals.

Summary table

| Example No. | 1* | 2* | 3 | 4 | 5* | 6 | 7 | 8* |
|---|---|---|---|---|---|---|---|---|
| Support | W/O emulsion stick | W/O emulsion | Aqueous solution | O/W emulsion | W/O emulsion | Aqueous solution | O/W emulsion | Aerosol W/O emulsion fluid |
| % Alum by weight/ amount of water | 33.3% | 13.6% | 13.6% | 13.6% | 22% | 22% | 22% | 22.4% |
| Presence of alum crystals | NO | NO | YES | YES | NO | YES | YES | NO |

(*)Example according to the invention

What is claimed is:

1. A deodorant composition comprising a water-in-oil emulsion comprising an aqueous phase, a fatty phase, and an effective amount of at least one alum salt dissolved in the aqueous phase of said emulsion.

2. The composition according to claim 1, wherein said at least one alum salt is chosen from:
   potassium alum, of structure: $KAl(SO_4)_2 \cdot 12H_2O$,
   ammonium alum, of structure: $NH_4Al(SO_4)_2 \cdot 12H_2O$,
   sodium alum, of structure: $NaAl(SO_4)_2 \cdot 12H_2O$, and
   aluminium sulphate salts of structure: $Al_2(SO_4)_3 \cdot nH_2O$ in which n is from 0 to 27.

3. The composition according to claim 1, wherein said at least one alum salt is chosen from alum salts with a solubility of less than 30 g/100 ml of water at 20° C.

4. The composition according to claim 3, wherein said at least one alum salt is chosen from alum salts with a solubility of less than 13 g/100 ml of water at 20° C.

5. The composition according to claim 1, wherein said at least one alum salt is potassium alum.

6. The composition according to claim 1, wherein said at least one alum is dissolved in the aqueous phase of said emulsion in an amount ranging from 0.5 to 30% by weight relative to the total weight of the composition.

7. The composition according to claim 6, wherein said at least one alum is dissolved in the aqueous phase in an amount greater than 10% by weight relative to the total weight of the composition.

8. The composition according to claim 1, wherein said at least one alum is dissolved in the aqueous phase in an amount greater than 10% by weight relative to the total weight of the composition.

9. The composition according to claim 8, wherein said at least one alum is dissolved in the aqueous phase in a concentration of greater than or equal to 15% by weight relative to the total weight of the composition.

10. The composition according to claim 7, wherein said at least one alum is dissolved in the aqueous phase in a concentration of greater than or equal to 15% by weight relative to the total weight of the composition.

11. The composition according to claim 1, wherein the fatty phase of said emulsion comprises an ingredient chosen from oils and waxes.

12. The composition according to claim 11, wherein the oils are chosen from mineral oils, plant oils, synthetic oils, fluoro oils, perfluoro oils, polyalkylenes, and volatile and non-volatile silicone oils.

13. The composition according to claim 11, wherein the waxes are chosen from animal, fossil, plant, mineral and synthetic waxes, hydrogenated castor oil, paraffins and silicone waxes and resins.

14. The composition according to claim 1, wherein the fatty phase is present in said composition in weight concentrations ranging from 5% to 80% relative to the total weight of the composition.

15. The composition according to claim 14, wherein the fatty phase concentration ranges from 10% to 50% relative to the total weight of the composition.

16. The composition according to claim 1, wherein the aqueous phase further comprises an additional ingredient chosen from wetting agents, stabilizers and sequestering agents.

17. The composition according to claim 1, wherein said composition further comprises at least one W/O emulsifying surfactant with an HLB of less than or equal to 6.

18. The composition according to claim 17, wherein the at least one W/O emulsifying surfactant is chosen from fatty acid esters of glucose; fatty acid esters of glycerol; fatty acid esters of sorbitol; and polyalkylpolyethersiloxanes bearing polyoxyalkylenated groups grafted onto the main silicone chain.

19. The composition according to claim 17, wherein the at least one W/O emulsifying surfactant is chosen from the polydiorganosiloxanes of formulae (I) and (II) below, wherein said polydiorganosiloxanes can be dispersed in a volatile dimethicone,

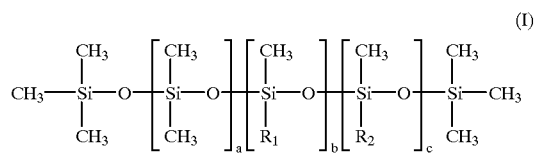

(I)

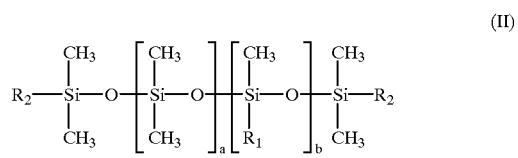

(II)

in which:
R$_1$ is chosen from linear and branched C$_{12}$–C$_{20}$ alkyl;
R$_2$ is chosen from —C$_n$H$_{2n}$—(—OC$_2$H$_4$—)$_x$—(—OC$_3$H$_6$—)$_y$—O—R$_3$,
R$_3$ is chosen from a hydrogen atom and linear and branched alkyl radicals comprising from 1 to about 12 carbon atoms,
a is an integer ranging from 0 to about 500, b is an integer ranging from 0 to about 500,
c is an integer ranging from 0 to about 500,
n is an integer ranging from 2 to 12,
x and y are each an integer ranging from 0 to about 50, wherein the sum x+y is greater than or equal to the value 1.

20. The composition according to claim 19, wherein the at least one W/O emulsifier is a polymer of formula (I) in which a is an integer ranging from 2 to 450, b is 0, c is an integer ranging from 2 to 40, n is an integer ranging from 2 to 5, x is an integer ranging from x to 30, and y is an integer ranging from 0 to 30, with $x \geq y$.

21. The composition according to claim 17, wherein the at least one W/O emulsifier is a mixture comprising cyclomethicone and dimethicone copolyol.

22. The composition according to claim 19, wherein the at least one W/O emulsifier is a polymer of formula (I) in which a is 0 and b is other than 0.

23. The composition according to claim 17, wherein the at least one W/O emulsifier is chosen from laurylmethicone copolyol and cetyldimethicone copolyol.

24. The composition according to claim 19, wherein R1 is chosen from $C_{12}$–$C_{18}$ alkyls.

25. The composition according to claim 17, wherein the at least one W/O emulsifying surfactant is present in weight proportions ranging from about 0.1% to about 10%.

26. The composition according to claim 25, wherein the at least one W/O emulsifying surfactant is present in weight proportions ranging ranging from about 1% to about 8% relative to the total weight of the composition.

27. The composition according to claim 1, wherein said composition further comprises at least one additional deodorant active agent in addition to the alum.

28. The composition according to claim 27, in which the at least one additional deodorant active agent is chosen from aluminium salts, zirconium salts, sodium bicarbonate, bacteriostatic agents, bactericides, odor-absorbing substances and antioxidants.

29. The composition according to claim 1, wherein said composition further comprises cosmetic adjuvants chosen from organic solvents, gelling agents, emollients, softeners, antioxidants, opacifiers, stabilizers, silicones, antifoaming agents, hydrating agents, vitamins, fragrances, preserving agents, surfactants, fillers, polymers, propellants, acidifying or basifying agents, dyes, pigments, and thickeners.

30. The composition according to claim 1 wherein said composition is in the form of a lotion, a cream or a fluid gel dispensed as an aerosol spray, in a pump-dispenser bottle or as a roll-on; or said composition is in the form of thickened cream dispensed in tubes; or in the form of a stick.

31. A cosmetic or dermatological deodorant formulation, comprising a water-in-oil emulsion comprising an aqueous phase, a fatty phase, and an effective amount of at least one alum salt dissolved in the aqueous phase of said emulsion.

32. A process for making a cosmetic or a dermatological product intended for treating human underarm odors, comprising the step of including in said product a water-in-oil emulsion comprising an aqueous phase, a fatty phase, and an effective amount of at least one alum salt dissolved in the aqueous phase of said emulsion.

33. A process for treating human underarm odors, comprising applying an effective amount of a deodorant composition to the armpit area, said deodorant composition comprising a water-in-oil emulsion comprising an aqueous phase, a fatty phase, and an effective amount of at least one alum salt dissolved in the aqueous phase of said emulsion.

34. A process for the manufacture of a maintenance product or a deodorant, comprising the step of including in said product a water-in-oil emulsion comprising an aqueous phase, a fatty phase, and an effective amount of at least one alum salt dissolved in the aqueous phase of said emulsion.

35. A process for the manufacture of a cosmetic or a dermatological aqueous deodorant product containing an alum salt in dissolved form, comprising the step of dissolving said alum salt in an aqueous phase of a water-in-oil emulsion further comprising a fatty phase.

36. The process according to claim 35, wherein said alum salt is dissolved in the aqueous phase in an amount greater than 10% by weight relative to the total weight of the composition.

37. The process according to claim 36, wherein said alum salt is dissolved in the aqueous phase in an amount greater than or equal to 15% by weight relative to the total weight of the composition.

* * * * *

UNITED STATES PATENT AND TRADEMARK OFFICE
CERTIFICATE OF CORRECTION

PATENT NO.     : 6,139,824

DATED:         : October 31, 2000

INVENTORS:     : Delphine Ribery et al.

It is hereby certified that errors appear in the above-identified patent and that said Letters Patent is hereby corrected as shown below:

In Claim 19, column 11, line 2, delete "0 to about 500" and insert --1 to about 500--;

In Claim 20, column 11, line 11, delete "x to 30" and insert --1 to 30--;

In Claim 26, column 11, line 29, delete "ranging" (second occurrence).

Signed and Sealed this

Twenty-fourth Day of April, 2001

Attest:

NICHOLAS P. GODICI

Attesting Officer    Acting Director of the United States Patent and Trademark Office